(12) United States Patent
Song et al.

(10) Patent No.: US 11,618,741 B2
(45) Date of Patent: Apr. 4, 2023

(54) METHOD FOR PREPARING DISELENIDE COMPOUND

(71) Applicant: SHANGHAI SPARK PHARMACEUTICAL CO., LTD., Shanghai (CN)

(72) Inventors: Kunyuan Song, Shanghai (CN); Weiwei Chen, Shanghai (CN)

(73) Assignee: SHANGHAI SPARK PHARMACEUTICAL CO., LTD., Shanghai (CN)

( * ) Notice: Subject to any disclaimer, the term of this patent is extended or adjusted under 35 U.S.C. 154(b) by 36 days.

(21) Appl. No.: 17/290,894

(22) PCT Filed: Jun. 18, 2020

(86) PCT No.: PCT/CN2020/096834
§ 371 (c)(1),
(2) Date: May 3, 2021

(87) PCT Pub. No.: WO2021/217825
PCT Pub. Date: Nov. 4, 2021

(65) Prior Publication Data
US 2022/0081405 A1    Mar. 17, 2022

(30) Foreign Application Priority Data
Apr. 30, 2020  (CN) .......................... 202010363063.9

(51) Int. Cl.
*C07D 311/32*  (2006.01)
(52) U.S. Cl.
CPC .................. *C07D 311/32* (2013.01)
(58) Field of Classification Search
CPC .................................................. C07D 311/32
See application file for complete search history.

(56) References Cited

U.S. PATENT DOCUMENTS

| | | | | |
|---|---|---|---|---|
| 6,025,387 A | * | 2/2000 | Yoo ...................... | C07D 311/30 549/288 |
| 2014/0323745 A1 | * | 10/2014 | Chen .................... | C07D 329/00 549/400 |

FOREIGN PATENT DOCUMENTS

| | | |
|---|---|---|
| CN | 103191121 A | 7/2013 |
| CN | 103191121 B | 9/2015 |
| CN | 105130864 A | 12/2015 |
| CN | 110627761 A | 12/2019 |
| CN | 112479959 A | 3/2021 |

OTHER PUBLICATIONS

Fengshou Tian, et al., "Progress in the synthesis of selenoethers," Chemical Reagents, Dec. 31, 2007 Issue 8 vol. 29 ISSN: 0258-3283 p. 469-473 (6 pages).

* cited by examiner

*Primary Examiner* — Valerie Rodriguez-Garcia
(74) *Attorney, Agent, or Firm* — Muncy, Geissler, Olds & Lowe, P.C.

(57) ABSTRACT

The present disclosure provides a method for preparing diselenide compound. A polar solvent is added to a dihydroflavonol compound, heated to 80° C.~100° C., kept for 40~50 minutes, then the base in the amount of 0.4~1.0 times the amount of the dihydroflavonol compound is added and reacted at 80° C.~100° C. for 5~60 minutes, then selenium dioxide in the amount of 0.6~1.2 times the amount of dihydroflavonol compounds at 80° C.~100° C. The diselenide compound of the dihydroflavonol compound is obtained by reacting at a temperature of 80° C.~100° C. for 30~150 minutes. The method of the present disclosure has mild reaction, low pollution, does not require an anhydrous and oxygen-free environment, and is suitable for large-scale industrial production.

5 Claims, 2 Drawing Sheets

Note: The solvent used for the 1H NMR and 13C NMR in this experiment is DMSO-d6.

MS analysis spectrum

METHOD FOR PREPARING DISELENIDE COMPOUND

BACKGROUND OF THE INVENTION

Technical Field of the Invention

The present disclosure relates to the technical field of organic synthesis, and specifically relates to a method for preparing diselenide compound.

Background

Selenium is a trace element necessary for the human body with various biological activities such as anti-oxidation, anti-cancer, anti-cancer, protection of bone marrow hematopoiesis, and delaying aging, and also has detoxifying effects on some heavy metal elements (such as mercury, arsenic, silver, etc.). There are two sources of selenium intake in the human body, one is inorganic and one is organic. Inorganic selenium generally refers to sodium selenite and sodium selenate, including yeast selenium and malt selenium with significant inorganic selenium residues. Inorganic selenium has greater toxicity and is not easily absorbed, making it unsuitable for human and animal use. Organic selenium includes simple selenoethers, diselenoethers and oxides of organic selenium. Compared with inorganic selenium, organic selenium has the characteristics of high bioavailability, strong biological activity, low toxicity and low environmental pollution. The organic selenium compounds synthesized in recent years, such as selenized chitosan, selenoproteins, selenopolysaccharides, selenized carrageenan, selenized tea polyphenols and other selenium small molecules or biomacromolecular compounds, are significantly higher than the corresponding compounds without selenization in terms of biological activities such as anti-tumor, treatment of cardiovascular diseases, anti-aging and improving the immunity of the body. Plant-active selenium is a permitted source of selenium for humans and animals. The synthesis of organoselenium compounds with high biological activity and low toxicity using the unique chemical and biological properties of selenium has been one of the current hot spots in pharmaceutical research.

Diselenide molecules in organic selenium contain selenium-selenium bonds, most of which have very important biological activities, such as anti-oxidation, anti-virus, anti-cancer, and anti-cancer effects, and have broad application prospects in the field of medicine. They are also an important organic synthesis reagent, and they also have broad application prospects in the field of organic synthesis. Currently, the Grignard reagent method is the classical method for the synthesis of diselenide, but the method requires strict anhydrous and oxygen-free operating conditions and low temperature environment, the process is relatively cumbersome, the yield is not high, and it is also not suitable for substrates with functional groups such as carbonyl and nitro. The hydrazine hydrate reduction method can prepare diselenyl ethers in a simpler way, but the high temperature conditions limit the method to prepare only dihydrocarbon diselenyl ethers, which are not suitable for the preparation of diselenyl ethers containing functional groups. Transition metal catalysis, which was first reported by Singh et al. in 2010, was able to obtain high yield diselenide by reacting aryl halide with monoselenide at 90° C. for 1 hour under nitrogen protection with nano-copper oxide as catalyst and DMSO as solvent and KOH as base. The reaction uses nitrogen protection, toxic organic solvents and harsh reaction conditions. The rest of the methods basically involve the synthesis of a compound containing a selenium and then reacting to produce diselenide. For example, selenocarbonyl compounds are synthesized first, and then diselenyl ethers are synthesized. All these selenium transfer reagents are difficult to prepare and their applications are limited.

Patent CN 103191121 B discloses a method for synthesizing an anti-tumor drug bis(quinolin-4-yl)diselenide. Among them are used sodium diselenide, potassium diselenide or lithium diselenide reagents, which need to be prepared with sodium borohydride (NaBH$_4$) under oxygen-free conditions. The reaction of sodium borohydride is very intense, difficult to control, requires ice bath cooling, and is not easily produced on a large scale. The reaction of sodium diselenide with and 4-chloroquinoline also has to be reacted under anhydrous conditions, which are harsh.

SUMMARY OF INVENTION

The present disclosure is carried out to solve the above problems, and aims to provide a method for preparing diselenide compound with mild reaction, low pollution, no need for anhydrous and oxygen-free environment, and suitable for large-scale industrial production.

The present disclosure provides a method for preparing diselenide compound, which includes steps of: adding polar solvent to dihydroflavonol compound, heating to 80° C.~100° C., and keeping for 40~50 minutes; then adding base in the amount of 0.4~1.0 times the amount of the dihydroflavonol compound, reacting for 5~60 minutes at a temperature of 80° C.~100° C.; then adding selenium dioxide in the amount of 0.6~1.2 times the amount of the dihydroflavonol compound, reacting for 30~150 minutes at a temperature of 80° C.~100° C.; and obtaining diselenide compound of dihydroflavonol compound. The reaction equation is shown as below:

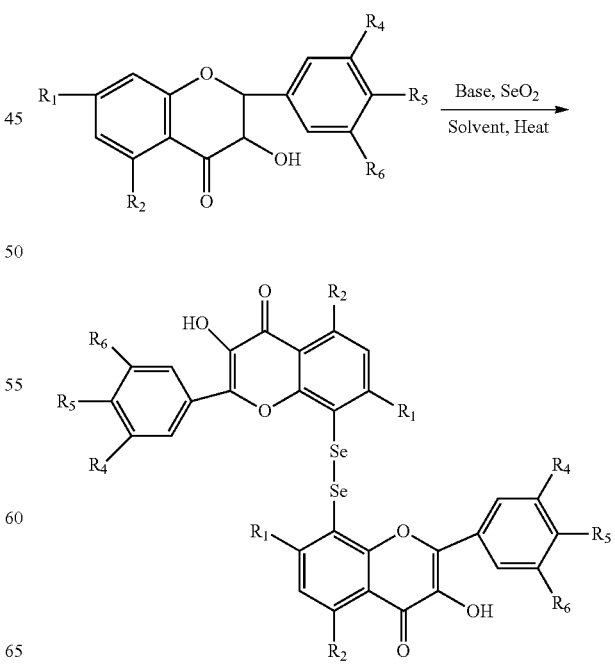

Further, the method provided by the present disclosure for preparing diselenide compound also include the feature that the dihydroflavonol compound has the general formula as below:

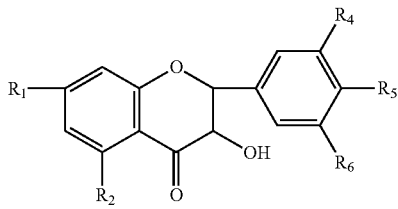

wherein $R_1$ is —H, —OH, $CH_3O$—, $CH_3CH_2O$—, $(CH_3)_3CO$—, $C_6H_6CH_2O$—, a variety of glycosides and so on; $R_2$ is —H, —OH, $CH_3O$—, $CH_3CH_2O$—, $(CH_3)_3CO$—, $C_6H_6CH_2O$—, a variety of glycosides and so on; $R_4$ is —H, —OH, $CH_3O$—, $CH_3CH_2O$—, $(CH_3)_3CO$—, $C_6H_6CH_2O$—, a variety of glycosides and so on; $R_5$ is —H, —OH, $CH_3O$—, $CH_3CH_2O$—, $(CH_3)_3CO$—, $C_6H_6CH_2O$—, a variety of glycosides and so on; $R_6$ is —H, —OH, $CH_3O$—, $CH_3CH_2O$—, $(CH_3)_3CO$—, $C_6H_6CH_2O$—, a variety of glycosides and so on.

Further, the method for preparing diselenide compound provided by the present disclosure also have the feature that the polar solvent is water or methanol or ethanol.

Further, the method for preparing diselenide compound provided by the present disclosure also have the feature that the dihydroflavonol compound includes the racemate, 2S,3S isomer, and 2R,3R isomer of the dihydroflavonol compound. The 2S,3S isomer of the dihydroflavonol compound has the general formula as below:

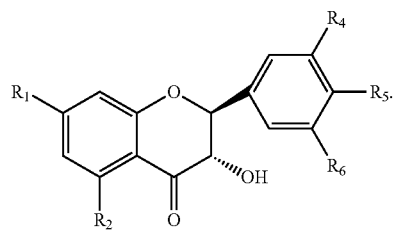

The general formulas of the 2R,3R isomers of dihydroflavonol compound is as follows:

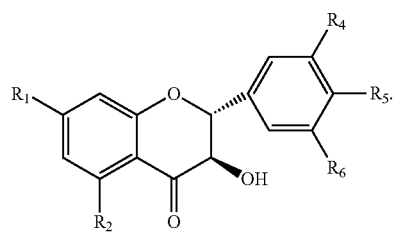

Further, in the method for preparing diselenide compound provided by the present disclosure also have the feature that the diselenide compound is obtained by naturally cooling to room temperature after the reaction is completed, adjusting the pH value of the reaction solution to 3~6.5, extracting, separating by column chromatography, and lyophilizing.

The present disclosure provides the following advantages:

The method for preparing diselenide compound involved in the present disclosure has mild reaction conditions and is carried out below 100° C., does not require an anhydrous and oxygen-free environment, and the reaction is stable and easy to control; the preparation process has little pollution, simple post-treatment, and simple operation; the raw materials are cheap and easy to obtain, suitable for large-scale industrial production.

BREIF DESCRIPTION OF THE DRAWINGS

DETAILED DESCRIPTION OF THE INVENTION

Figure 1:
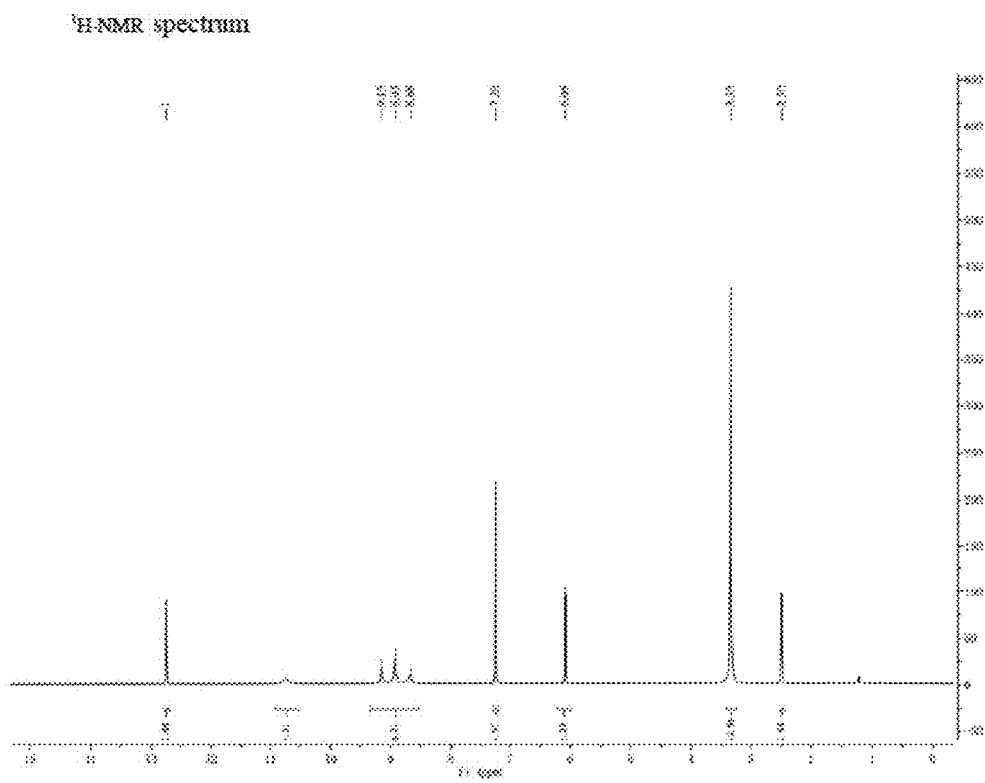
FIG. 1 is a 1H nuclear magnetic resonance (NMR) spectrum of the product in Example 1 of the present disclosure.

In order to make the technical means, creative features, achieved purpose and efficacy realized by the present disclosure easy to understand, the method of preparing diselenide compound of the present disclosure is specified below in conjunction with the embodiments.

EXAMPLE 1

In this embodiment, dihydromyricetin was selected as the dihydroflavonol compound, which has the following general formula:

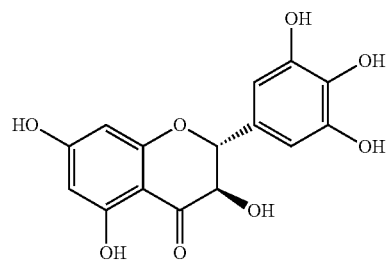

22.5 g of dihydromyricetin was added into a four-necked flask (specification 500 mL), 200 mL of water was added, heated to 80° C., and kept for 45 minutes. 2.81 g of sodium hydroxide was added, and reacted for 10 minutes under the temperature being controlled at 80° C., and 7.80 g of selenium dioxide was added and reacted for 70 minutes under the temperature being controlled at 80° C., and then the reaction was complete. Then, the heating was turned off, the pH was adjusted to 3~6.5 with hydrochloric acid after naturally cooling to room temperature, and methanol was used for extraction. Dimyricetin-based diselenide product was obtained by lyophilizing after column chromatography separation, the yield was 8.63%.

EXAMPLE 2

In this embodiment, dihydromyricetin was selected as the dihydroflavonol compound, which has the following general formula:

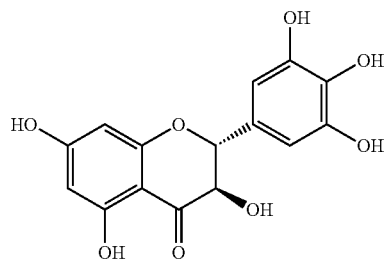

15 g of dihydromyricetin was added into a four-necked flask (specification 500 mL), 200 mL of water was added, heated to 90° C., and kept for 45 minutes. 0.75 g of sodium hydroxide was added, and reacted for 60 minutes under the temperature being controlled at 90° C., and 4.16 g of selenium dioxide was added and reacted for 70 minutes under the temperature being controlled at 90° C., and then the reaction was completed. Then, the heating was turned off, the pH was adjusted to 3-6.5 with hydrochloric acid after naturally cooling to room temperature after, and methanol was used for extraction. Dimyricetin-based diselenide product was obtained by lyophilizing after column chromatography separation, the yield was 10.26%.

EXAMPLE 3

In this embodiment, dihydromyricetin is selected as the dihydroflavonol compound, which has the following general formula:

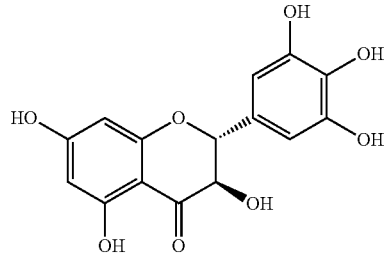

22.5 g of dihydromyricetin was added into a four-necked flask (specification 500 mL), 200 mL of water was added, heated to 100° C., and kept for 45 minutes. 2.53 g of sodium hydroxide was added and reacted for 40 minutes under the temperature being controlled at 100° C., and 9.36 g of selenium dioxide was added and reacted for 30 minutes under the temperature being controlled at 100° C., and then the reaction was complete. Then, the heating was turned off, the pH was adjusted to 3~6.5 with hydrochloric acid after naturally cooling to room temperature, and methanol was used for extraction. Dimyricetin-based diselenide product was obtained by lyophilizing after column chromatography separation, the yield was 9.86%.

EXAMPLE 4

In this embodiment, dihydromyricetin was selected as the dihydroflavonol compound, which has the following general formula:

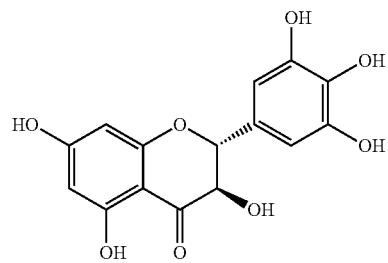

22.5 g of dihydromyricetin was added into a four-necked flask (specification 500 mL), 200 mL of water was added, heated to 90° C., and kept for 40 minutes. 1.69 g of sodium hydroxide was added and reacted for 20 minutes under the temperature being controlled at 90° C., and 6.24 g of selenium dioxide was added and reacted for 60 minutes under the temperature being controlled at 90° C., and then the reaction was complete. Then, the heating was turned off, the pH was adjusted to 3~6.5 with hydrochloric acid after naturally cooling to room temperature, and methanol was used for extraction. Dimyricetin-based diselenide product was obtained by lyophilizing after column chromatography separation, the yield was 20.2%.

EXAMPLE 5

In this embodiment, dihydromyricetin was selected as the dihydroflavonol compound, which has the following general formula:

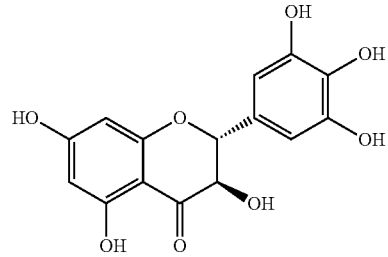

22.5 g of dihydromyricetin was added into a four-necked flask (specification 500 mL), 200 mL of water was added, heated to 90° C., and kept for 50 minutes. 2.36 g of sodium hydroxide was added and reacted for 50 minutes under the temperature being controlled at 90° C., and 6.24 g of selenium dioxide was added and reacted for 80 minutes under the temperature being controlled at 90° C., and then the reaction was complete. Then, the heating was turned off, the pH was adjusted to 3~6.5 with hydrochloric acid after naturally cooling to room temperature, and methanol was used for extraction. Dimyricetin-based diselenide product was obtained by lyophilizing after column chromatography separation, the yield was 21.75%.

EXAMPLE 6

In this embodiment, dihydromyricetin was selected as the dihydroflavonol compound, which has the following general formula:

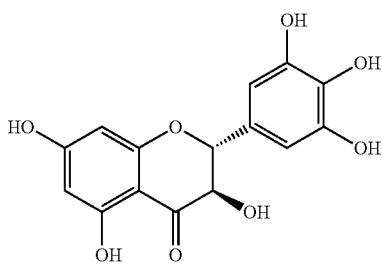

22.5 g of dihydromyricetin was added into a four-necked flask (specification 500 mL), 200 mL of water was added, heated to 95° C., and kept for 45 minutes. 4.05 g of sodium tert-butoxide was added and reacted for 20 minutes under the temperature being controlled at 95° C., and 4.69 g of selenium dioxide was added and reacted for 70 minutes under the temperature being controlled at 95° C., and then the reaction was complete. Then, the heating was turned off, the pH was adjusted to 3~6.5 with hydrochloric acid after naturally cooling to room temperature, and methanol was used for extraction. Dimyricetin-based diselenide product was obtained by lyophilizing after column chromatography separation, the yield was 13%

EXAMPLE 7

In this embodiment, dihydromyricetin was selected as the dihydroflavonol compound, which has the following general formula:

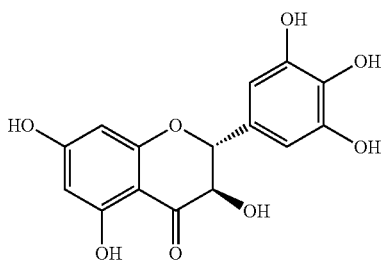

22.5 g of dihydromyricetin was added into a four-necked flask (specification 500 mL), 200 mL of water was added, heated to 90° C., and kept for 45 minutes. 4.05 g of sodium tert-butoxide was added and reacted for 5 minutes under the temperature being controlled at 90° C., and 6.24 g of selenium dioxide was added and reacted for 150 minutes under the temperature being controlled at 90° C., and then the reaction was complete. Then, the heating was turned off, the pH was adjusted to 6~6.5 with hydrochloric acid after naturally cooling to room temperature, and methanol was used for extraction. Dimyricetin-based diselenide product was obtained by lyophilizing after column chromatography separation, the yield was 38%.

The products obtained in the above seven embodiments were analyzed by NMR and mass (MS) spectrometry, respectively. All of them were verified to be dimyricetin-based diselenide. Only the MS spectrum, 1H NMR spectrum and 13C spectrum measured in Example 1 are listed below.

According to the 1H NMR spectrum shown in FIG. 1, the 1H NMR spectrum data of the product are as follows:

1H NMR (400 MHZ, DMSO-d6): δ 12.73(s,1H), 10.7(s, 1H) 9.15(s,1H), 8.93 (S,2H), 8.68(s, 1H), 7.26 (S,2H), 6.08(s,1H).

Figure 2:
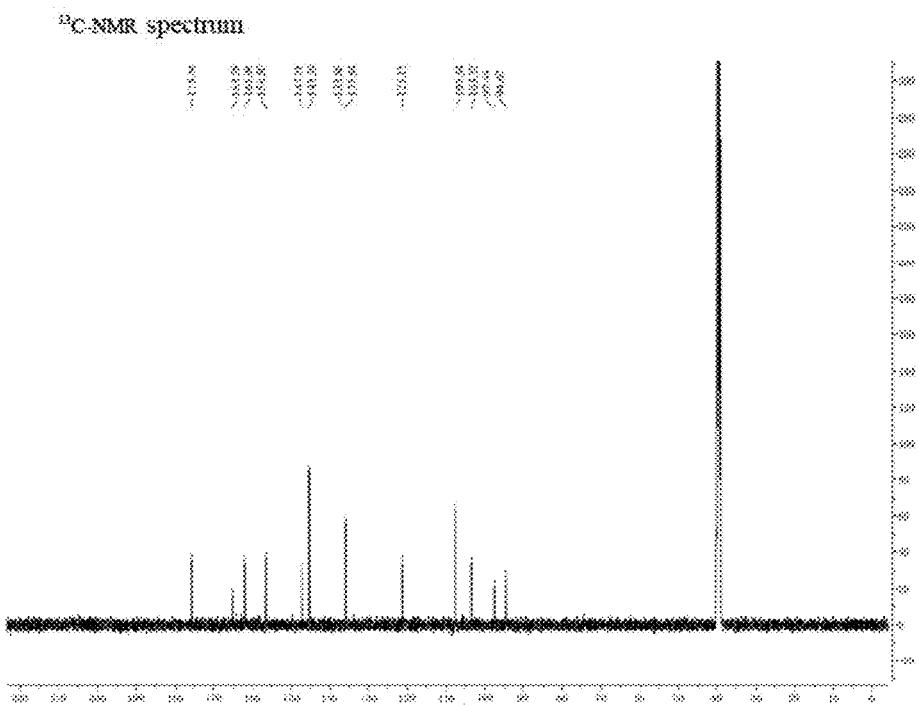
FIG. 2 is a 13C nuclear magnetic resonance (NMR) spectrum of the product in Example 1 of the present disclosure.

According to the 13C NMR spectrum shown in FIG. 2, the data of the 13C NMR spectrum of the product is as follows:

13C NMR (400 MHZ, DMSO-d6): δ 175.95, 166.25, 162.39, 156.95, 147.55, 145.87, 145.87, 136.30, 136.30, 121.63, 107.97, 107.97, 103.67, 98.14, 95.00.

Figure 3:
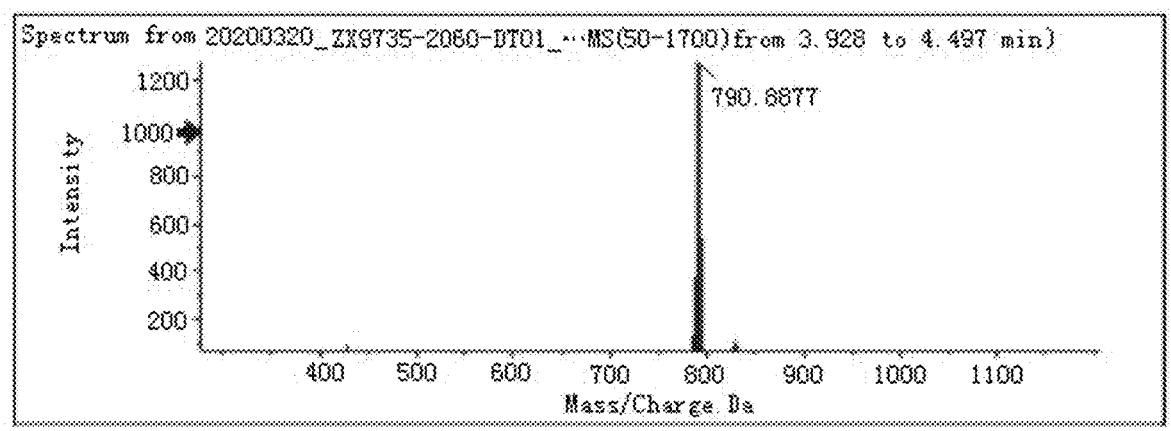
FIG. 3 is a mass spectrum of the product in Example 1 of the present invention.

According to the MS spectrum shown in FIG. 3, the highest molecular ion peak is 790.887, and selenium has multiple isotope peaks.

From the information provided by the 1H NMR spectrum, 13C NMR spectrum and MS spectrum, it can be seen that the product obtained is dimyricetin-based diselenide.

EXAMPLE 8

In this embodiment, dihydroflavonol was selected as the dihydroflavonol compound, which has the following general formula:

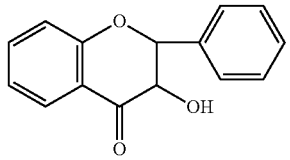

22.5 g of dihydroflavonol was added into a four-necked flask (specification 500 mL), 200 mL of 30% methanol was added, heated to 90° C., and kept for 45 minutes. 3.62 g of sodium hydroxide was added and reacted for 40 minutes under the temperature being controlled at 90° C., and 9.24 g of selenium dioxide was added and reacted for 70 minutes under the temperature being controlled at 90° C., and then the reaction was complete. Then, the heating was turned off, the pH was adjusted to 5~6 with hydrochloric acid after naturally cooling to room temperature, and methanol was used for extraction. Dihydroflavonol diselenide product was obtained by lyophilizing after column chromatography separation, the yield was 12.6%.

The resulting products were analyzed by NMR and mass spectrometry, respectively, and the analysis confirmed that the product is dihydroflavonol diselenide.

The method for preparing diselenide compound related to the present disclosure is not limited to the scope of specific embodiments. The above content is only a basic description of the present disclosure, and any equivalent transformations made based on the technical solutions of the present disclosure shall fall within the scope of protection of the present disclosure.

The invention claimed is:

1. A method for preparing a diselenide compound of a dihydrofalvonol compound, comprising steps of:
adding polar solvent to dihydroflavonol compound, heating to 80° C.~100° C., and keeping for 40~50 minutes;
then adding base in the amount of 0.4~1.0 times the amount of the dihydroflavonol compound, reacting for 5~60 minutes at a temperature of 80° C.~100° C.;

then adding selenium dioxide in the amount of 0.6~1.2 times the amount of the dihydroflavonol compound, reacting for 30~150 minutes at a temperature of 80° C.~100° C.; and obtaining the diselenide compound of the dihydroflavonol compound.

2. The method for preparing the diselenide compound according to claim 1, wherein the dihydroflavonol compound is of the following formula:

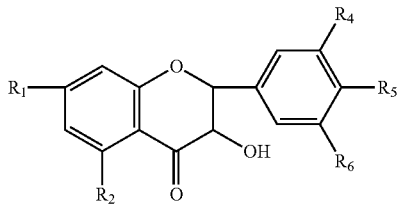

wherein $R_1$ is —H, —OH, $CH_3O$—, $CH_3CH_2O$—, $(CH_3)_3CO$—, $C_6H_6CH_2O$—, or a glycoside; $R_2$ is —H, —OH, $CH_3O$—, $CH_3CH_2O$—, $(CH_3)_3CO$—, $C_6H_6CH_2O$—, or a glycoside; $R_4$ is —H, —OH, $CH_3O$—, $CH_3CH_2O$—, $(CH_3)_3CO$—, $C_6H_6CH_2O$—, or a glycoside; $R_5$ is —H, —OH, $CH_3O$—, $CH_3CH_2O$—, $(CH_3)_3CO$—, $C_6H_6CH_2O$—, or a glycoside; $R_6$ is —H, —OH, $CH_3O$—, $CH_3CH_2O$—, $(CH_3)_3CO$—, $C_6H_6CH_2O$—, or a glycoside.

3. The method for preparing the diselenide compound according to claim 1, wherein the polar solvent is water, methanol or ethanol.

4. The method for preparing the diselenide compound according to claim 1, wherein the dihydroflavonol compound comprises racemates, 2S,3S isomers, and 2R,3R isomers of the dihydroflavonol compound.

5. The method for preparing the diselenide compound according to claim 1, wherein the diselenide compound is obtained by naturally cooling to room temperature after the reaction is completed, adjusting the pH value of the reaction solution to 3~6.5, extracting, separating by column chromatography, and lyophilizing.

* * * * *